United States Patent [19]

Chiao et al.

[11] Patent Number: 4,663,075
[45] Date of Patent: May 5, 1987

[54] NOVEL GELLING COMPOSITION

[75] Inventors: Wen B. Chiao, Piscataway; Dilip K. Ray-Chaudhuri, Bridgewater, both of N.J.

[73] Assignee: National Starch and Chemical Corporation, Bridgewater, N.J.

[21] Appl. No.: 805,074

[22] Filed: Dec. 4, 1985

Related U.S. Application Data

[62] Division of Ser. No. 550,327, Nov. 10, 1983, abandoned.

[51] Int. Cl.$^4$ .............................................. B01J 13/00
[52] U.S. Cl. ............................ 252/315.3; 252/315.1; 260/DIG. 31; 524/916
[58] Field of Search .................... 252/315.1, 315.3; 260/DIG. 31; 524/916

[56] References Cited

U.S. PATENT DOCUMENTS 3,898,165  8/1975  Ely et al. ............... 252/315.3 X
4,176,118 11/1979  Petinaux ..................... 260/239

FOREIGN PATENT DOCUMENTS 0213074 12/1983  Japan ....................... 252/315.1
1542393  3/1979  United Kingdom .
1550086  8/1979  United Kingdom .

OTHER PUBLICATIONS

"The Sulfonation of Aromatic Isocyanates: Sylfonated p-Tolyl Isocyanate-An X-Ray Structure Analysis", Gerhard Balle et al., Angew Chem. Int. Ed. Engl. 21, No. 11 (1982), pp. 867-888.

Primary Examiner—Richard D. Lovering
Attorney, Agent, or Firm—Lori D. Tolly; Edwin M. Szala

[57] ABSTRACT

Novel gelling agents are prepared by reacting diphenyldiisocyanates with sulfur trioxide in a molar concentration of about 1:2. When the sulfonated diphenyldiisocyanate is added to water in concentrations above 2%, a gel is produced which is stable under acidic conditions at pH levels of about 4 or less.

20 Claims, No Drawings

NOVEL GELLING COMPOSITION

This application is a division of application Ser. No. 550,327, filed Nov. 10, 1983, and now abandoned.

BACKGROUND OF THE INVENTION

This invention relates to novel sulfonated diphenyldiisocyanates. In a further aspect, this invention relates to novel gels produced from the sulfonated diphenyldiisocyanates upon their addition to water. These novel gels are stable under acidic conditions and at elevated temperatures.

It is known that sulfonation of various aromatic mono- and poly-isocyanates yields compounds containing both isocyanate and sulfonic acid functionalities on one molecule wherein the sulfo group exclusively enters at the ortho position to the isocyanate group on the aromatic ring. This position is favored due to the formation of a six-membered heterocyclic ring by the ortho sulfonic acid group with the isocyanate group, referred to as a cyclic carbamic acid-sulfonic acid anhydride. See Angew. Chem. Int. Ed. Eng. 21, No. 11 (1982), pgs. 867–868.

U.S. Pat. No. 4,176,118 issued Nov. 27, 1979 to M. Petinaux et al. describes the partial sulfonation of 4,4'-diphenyl diisocyanates which yields exclusively tetranuclear uretdione diisocyanate disulfonic acids. The reaction is carried out employing molar ratios in the range of from about 1:1 to about 1:1.4 of diisocyanate to $SO_3$ reagent, however it is disclosed that larger amounts of $SO_3$ may be used without substantially altering the course of the reaction. The compositions of Petinaux et al. are described as being useful as crosslinking agents as well as useful in the polymer synthesis of, for example, polyisocyanurates, polycarbodiimides, polyimides, and polyurethanes.

Neither of the above references disclose or suggest the novel compositions of the present invention or the unique gel forming ability they possess upon addition to water.

SUMMARY OF THE INVENTION

According to this invention sulfonated diphenyldiisocyanates are obtained as crystalline solids when isocyanates of the formula

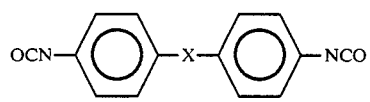

wherein X represents

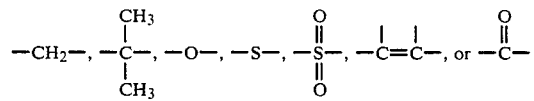

are sulfonated with sulfur trioxide in about a 1:2 molar ratio of diisocyanate to $SO_3$ at temperatures of from $-30°$ to $+100°$ C., preferably $10°$ to $30°$ C., in anhydrous solvents which are inert towards $SO_3$ and isocyanate groups. Furthermore, the present invention relates to the gel produced by the addition of these compositions to water and the novel properties of the gel.

DESCRIPTION OF THE PREFERRED EMBODIMENTS

The diphenyldiisocyanates useful herein have the general formula

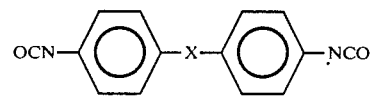

wherein X is defined above. These diisocyanates may be sulfonated by procedures commonly known in the art. Sulfur trioxide or other sulfur-containing materials capable of rendering $SO_3$ available may be employed. Use of sulfur trioxide is preferred. Accordingly, the diphenyldiisocyanates are treated with sulfur trioxide in a molar concentration of about 2 moles of sulfur trioxide to one mole of diisocyanate.

The sulfonation is carried out in a solvent which must be chemically inert to both $SO_3$ and the diisocyanates under the reaction conditions employed. Suitable solvents for the present invention include various halogenated hydrocarbons, dioxane, and tetrahydrofuran. The preferred solvent is 1,2-dichloroethane.

A typical sulfonation procedure useful herein involves simultaneously adding sulfur trioxide and a solution containing the diisocyanate and the inert solvent to a reaction vessel already charged with the solvent and purged with nitrogen. The reactants are introduced by slow addition being careful to keep the reaction temperature below $30°$ C. in order to achieve a uniform reaction with a controlled exotherm. The resultant sulfonated product precipitates from solution and may then be recovered in quantitative yields by filtration.

As described in the Angew. Chem. reference mentioned above, sulfonated isocyanates exist in equilibrium in the form of the cyclic carbamic acid-sulfonic acid anhydride or in the open form. In a similar fashion, the proposed structures of the sulfonated diphenyldiisocyanates herein, existing in equilibrium are

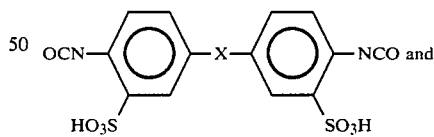

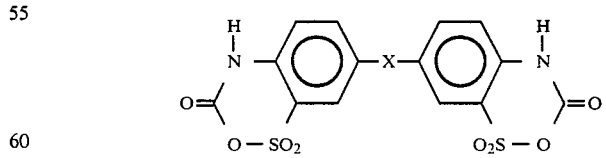

wherein X has been previously described. These structures are consistent with elemental analysis results. Upon addition to water, the sulfonated compositions are believed to hydrolyze, with the evolution of carbon dioxide, to form zwitterions consisting of amino and sulfonic acid functionalities having the formula

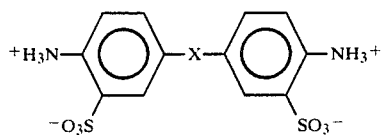

wherein X is described above.

It has been discovered that the sulfonated diphenyldiisocyanates of the present invention form a gel upon addition to water when added in concentrations above 2%. The amount of time necessary for gelling to occur is a function of the concentration of the sulfonated diisocyanate in aqueous solution. Generally, solutions containing 5% or more of the sulfonated diisocyanate will gel in less than thirty minutes at room temperature.

In order to prepare the novel gelling agent herein, it is necessary to react a suitable diphenyldiisocyanate with $SO_3$ in molar concentrations of about 1 mole diisocyanate to 2 moles $SO_3$, or in other words about stoichiometric amounts of $SO_3$ to isocyanate concentration are necessary. When diisocyanate:$SO_3$ molar ratios as low as 1:1.5 or as high as 1:3 are reacted it was found that products without gel-forming capabilities are produced.

The sulfonated products described herein, when added to water in concentrations of about 5% will normally alter the pH of the water to about 2. Stability studies on the gels at various pH's were carried out by adjusting samples containing 5% sulfonated diisocyanate to pH values from 0.5 to 10. It was found that the gel formation was reversible and that gels were only stable under acidic conditions at pH levels of about 4 or less. While not wishing to be bound to any theory or mechanism, it is currently believed that at higher pH levels the hydrolyzed sulfonates carry a negative charge and as a result, the gel will not form due to charge repulsion between the molecules.

The novel gels are stable upon extended holding times at elevated temperatures. For instance, gels maintained at 70° C. for 12 hours remained firm showing no sign of instability.

Oftentimes gels may be sensitive to various salt or polymer impurities present in solution. The novel gels herein were found to be insensitive to salts containing monovalent cations as well as to synthetic and natural polymers. The gels were, however, sensitive to salts containing divalent or multivalent cations. Such cations destroyed gel formation and resulted in fluffy precipitates.

The sulfonated diisocyanates of the present invention are useful, for example, as thickeners in aqueous systems and as absorbants.

The examples which follow will further illustrate the embodiment of our invention. In the examples, all temperatures were given in degrees Celsius and all parts are given by weight unless otherwise indicated.

EXAMPLE 1

This example illustrates the preparation of sulfonated 4,4′-diisocyanato-diphenyl methane (MDI).

A five-liter Morton flask equipped with a stirrer, thermometer, addition funnels, condenser with drying tube and a gas inlet adapter was purged with nitrogen for 15 minutes. Seven hundred twenty five (725) grams of 1,2-dichloroethane (DCE) was added to the flask. Using two addition funnels, 81.4 grams of sulfur trioxide (1.00 mole) and 440 ml of MDI solution in DCE were added simultaneously while maintaining the internal temperature between 15°–20° C. The MDI solution which contained 125 grams MDI (0.5 mole) in DCE was added at a rate of 10 ml/minute. The sulfur trioxide was added at a rate of 1 ml/minute. The sulfonated MDI precipitated as it formed. After completing sulfonation, the sulfonated MDI was filtered and dried at 60° C. A total of 210 grams of the sulfonate, a pink powder, was collected.

Elemental analysis for $C_{15}H_{10}N_2O_8S_2$: Calculated: C, 43.9%; H, 2.4%; N, 6.8%; O, 31.3%; S, 15.6%. Found: C, 42.1%; H, 2.9%; N, 6.2%; O, 33.2%; S, 15.5%.

EXAMPLE 2

This example illustrates the gel forming capabilities of MDI sulfonate from Example 1 in water at various concentrations.

Aqueous solutions of MDI sulfonate were prepared at pH=2 and observed for gel formation. The results are given in Table I.

TABLE I

| Concentration of MDI Sulfonate Solution (%) | Gel Time |
| --- | --- |
| 2.0 | no gel formation on prolonged standing |
| 2.5 | 18 hours |
| 5.0 | 30 minutes |
| 10.0 | 5 minutes |

The gel time was reduced drastically as the concentration of MDI sulfonate was increased with no gel formation observed for solutions containing 2.0 % or less of the sulfonate.

EXAMPLE 3

This example illustrates the criticality of the molar ratio of sulfur trioxide to diisocyanate necessary to produce a composition which is gel-forming upon addition to water.

MDI was sulfonated with sulfur trioxide in molar ratios of 1 mole MDI and from 1 to 3 moles sulfur trioxide. The sulfonated MDI products were prepared as in Example 1. The products were added at a 2.5% addition level to water and compared with the sulfonated product of Example 1. Results shown in Table II indicate that only sulfonated diisocyanates prepared with about 2 moles of sulfur trioxide for every mole of diisocyanate will produce a composition which is gel-forming in water.

TABLE II

| Sample | Diisocyanate:$SO_3$ Molar Ratio | Solubility in Water |
| --- | --- | --- |
| A | 1:1 | not soluble |
|   |   | no gel formation |
| B | 1:1.5 | not soluble |
|   |   | no gel formation |
| C | 1:2 | soluble |
|   |   | formed gel upon standing |
| D | 1:3 | soluble initially |
|   |   | precipitated upon standing |
|   |   | no gel formation |

EXAMPLE 4

This example illustrates the inability of other sulfonated phenyl isocyanates to form gels upon addition to water.

Other typical phenyl isocyanates were sulfonated as in Example 1 employing stoichiometric amounts of sulfur trioxide according to the isocyanate content of the composition. The isocyanates sulfonated included: phenyl isocyanate, 3,3'-dimethyl-4,4'-biphenylene isocyanate, and Rubinate M (a mixture of 70 mole percent of diethylene triphenylene isocyanate and 30 mole percent of MDI available from Rubicon Chemicals).

The sulfonated samples were compared with sulfonated MDI of Example 1 by preparing 5% aqueous solutions of each at pH=2 to observe gel formation. Results after 4 hours standing are shown in Table III.

TABLE III

| Sulfonated Sample | Final Appearance of the Solution |
| --- | --- |
| phenyl isocyanate | brown powdery precipitate formed in water |
| 3,3'-dimethyl-4,4'-biphenylene isocyanate | brown powdery precipitate formed in water |
| Rubinate M | clear, brown solution |
| MDI | yellow, translucent gel |

The results show that only diphenyldiisocyanates herein have gel forming capabilities in water after solution.

EXAMPLE 5

This example illustrates the effect of added salts on the gel formation of the sulfonated diphenyldiisocyanates herein.

Aqueous solutions containing 5% sulfonated MDI from Example 1 and 10% of various salts were prepared at pH=2. The salts employed included those containing monovalent cations: LiCl, NaCl, KCl, Na$_2$SO$_4$ and NH$_4$Cl; and those containing divalent or multivalent cations: MgCl$_2$, CaCl$_2$, and Al$_2$(SO$_4$)$_3$.

The samples which contained salts with monovalent cations formed firm gels while the other samples produced mixtures containing fluffy precipitates.

EXAMPLE 6

This example illustrates the effect of added synthetic or natural polymers on the novel gel formation of the sulfonated diphenyldiisocyanates.

Aqueous solutions containing 5% sulfonated MDI from Example 1 and 1% of various polymers were prepared at pH=2. The polymers employed included: gelatinized corn starch, carboxymethyl cellulose, hydroxyethyl cellulose, sulfonated polystyrene, polyacrylamide and polyethylene oxide.

All samples produced gels indicating that natural and synthetic polymers have no detrimental effect on gel formation.

We claim:

1. A gel-forming composition having a pH less than 4 comprising (a) water and (b) an amount greater than 2 percent of a sulfonated diphenyldiisocyanate prepared by sulfonating a diphenyldiisocyanate of the formula

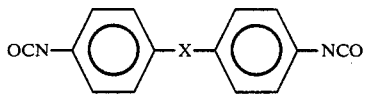

wherein X is

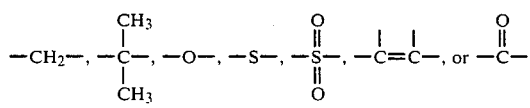

with sulfur trioxide in a molar ratio greater than 1:1.5 and less than 1:3 of the diphenyldiisocyanate to sulfur trioxide.

2. The composition of claim 1, which contains greater than 2 to 10 percent of the sulfonated diiphenyldiisocyanate.

3. The composition of claim 1, wherein the molar ratio of diphenyldiisocyanate to sulfur trioxide is about 1:2.

4. The composition of claim 1, wherein X is —CH$_2$—.

5. The composition of claim 4, wherein the sulfonated diphenyldiisocyanate has the formula C$_{15}$H$_{10}$N$_2$O$_8$S$_2$.

6. The composition of claim 1, further comprising a monovalent cation.

7. The composition of claim 6, wherein the monovalent cation is selected from the group consisting of Li$^+$, Na$^+$K$^+$ and NH$_4$$^+$.

8. The composition of claim 1, further comprising a synthetic or natural polymer.

9. The composition of claim 8, wherein the synthetic or natural polymer is selected from the group consisting of gelatinized starch, carboxymethyl cellulose, hydroxyethyl cellulose, sulfonated polystyrene, polyacrylamide and polyethylene oxide.

10. A process for the preparation of a gel comprising the step of forming a solution of water and greater than 2 percent of a sulfonated diphenyldiisocyanate at a pH less than 4.0 required for gel formation, the sulfonated diphenyldiisocyanate prepared by sulfonating a diphenyldiisocyanate of the formula

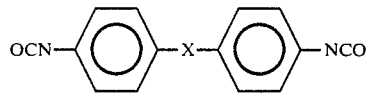

wherein X is

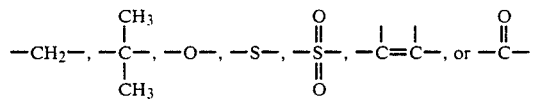

with sulfur trioxide in a molar ratio greater than 1:1.5 and less than 1:3 of the diphenyldiisocyanate to sulfur trioxide.

11. A process for the reversible reversal of the gel prepared in claim 10 comprising adjusting the pH of the gel to a value of at least 4.0.

12. The process of claim 10, wherein the solution is formed with greater than 2 to 10 percent of the sulfonated diphenyldiisocyanate.

13. The process of claim 10, wherein the molar ratio of diphenyldiisocyanate to sulfur trioxide is about 1:2.

14. The process of claim 10, wherein X is —CH$_2$—.

15. The process of claim 14, wherein the sulfonated diphenyldiisocyanate has the formula C$_{15}$H$_{10}$N$_2$O$_8$S$_2$.

16. The process of claim 10, further comprising adding a monovalent cation to the solution.

17. The process of claim 16, wherein the monovalent cation is selected from the group consisting of Li$^+$, Na$^+$, K$^+$ and NH$_4$$^+$.

18. The process of claim 10, further comprising adding a synthetic or natural polymer to the solution.

19. The process of claim 18, wherein the synthetic or natural polymer is selected from the group consisting of gelatinized starch, carboxymethyl cellulose, hydroxyethyl cellulose, sulfonated polystyrene, polyacrylamide and polyethylene oxide.

20. The gel produced by the process of claim 10.

* * * * *